US005550114A

United States Patent [19]
Strayer

[11] Patent Number: 5,550,114
[45] Date of Patent: Aug. 27, 1996

[54] EPIDERMAL GROWTH FACTOR INHIBITOR

[75] Inventor: David S. Strayer, Newton Square, Pa.

[73] Assignee: Thomas Jefferson University, Philadelphia, Pa.

[21] Appl. No.: 41,774

[22] Filed: Apr. 2, 1993

[51] Int. Cl.$^6$ ............... A61K 38/16; C07K 14/47; C07K 1/20; C07K 1/30
[52] U.S. Cl. ............... 514/21; 530/350; 530/399; 530/417
[58] Field of Search ............... 514/21; 530/399, 530/417, 350

[56] References Cited

U.S. PATENT DOCUMENTS

| | | | |
|---|---|---|---|
| 4,230,727 | 10/1980 | Nuss, Jr. et al. | 514/641 |
| 4,289,690 | 9/1981 | Pestka et al. | 530/412 |
| 4,462,986 | 7/1984 | Smith | 424/85.5 |
| 4,569,935 | 2/1986 | Rosenberg et al. | 514/252 |
| 4,606,917 | 8/1986 | Eppstein | 424/85.6 |
| 4,929,442 | 5/1990 | Powell | 424/85.2 |
| 4,997,929 | 3/1991 | Collins et al. | 435/69.1 |
| 5,126,323 | 6/1992 | Rogers et al. | 514/12 |
| 5,216,176 | 6/1993 | Heindel et al. | 549/280 |
| 5,242,921 | 9/1993 | Milstone et al. | 514/249 |

OTHER PUBLICATIONS

Sofer et al BioTechniques, Nov./Dec. 1983 pp. 198–203.

Laurence, D. J. R., Gusterson, B. A.: The Epidermal Growth Factor. *Tumor Biol.* (1990), 11:229–261.

Coleman, S., Silberstein, G. B., Daniel, C. W.: Ductal Morphogenesis in the Mouse Mammary Gland: Evidence Supporting a Role for Epidermal Growth Factor. *Dev. Biol.*, (1988), 127:304–315.

Taub, M., Wang, Y., Szcaesny, T. M., Kleinman, H. K.: Epidermal Growth Factor or Transforming Growth Factor α is Required for Kidney Tubulogenesis in Matrigel Cultures in Serum–Free Medium. *Proc. Natl. Acad. Sci.* (1990) 87:4002–4006.

Greenfield, C., Hiles, I., Waterfield, M. D., Federwisch, M., Wollmer, A., Blundell, T. L., McDonald, N.: Epidermal Growth Factor Binding Induces a Conformational Change in the External Domain of its Receptor. *EMBO J.*, (1989), 8:4115–4123.

Nickoloff, B. J., Mitra, R. S.: Inhibition of $^{125}$I–Epidermal Growth Factor Binding to Cultured Keratinocytes by Antiproliferative Molecules Gamma Interferon, Cyclosporin A, and Transforming Growth Factor–Beta. *J. Invest., Dermatol.* (1989), 93:799–803.

Imamoto, A., Beltran, L. M., DiGiovanni, J.: Differential Mechanism for the Inhibition of Epidermal Growth Factor Binding to its Receptor on Mouse Keratinocytes by Anthrones and Phorbol Esters. *Carcinogenesis* (1990), 11:1543–1549.

Hori, T., Kashiyama, S., Hayakawa, M., Shimbamoto, S., Tsujimoto, M., Oku, N., Ito, F.: Possible Role of Prostaglandins as Negative Regulators in Growth Stimulation by Tumor Necrosis Factor and Epidermal Growth Factor in Human Fibroblasts. *J. Cell. Physiol.* (1989), 141:275–280.

Murthy, U., Rieman, D. J., Rodeck, U.: Inhibition of TGF Alpha–Induced Second Messengers by Anti–EGF Receptor Anti–Body–425. *Biochem. Biophys. Res. Comm.* (1990), 172:471–476.

Rodeck, U., Williams, N., Murthy, U., Herlyn, M.: Monoclonal Antibody 425 Inhibits Growth Stimulation of Carcinoma Cells by Exopenous EGF and Tumor–Derived EGF–TGF–Alpha. *J. Cell. Biochem.* (1990), 44:69–79.

(List continued on next page.)

*Primary Examiner*—Mindy Fleisher
*Assistant Examiner*—Nancy J. Degen
*Attorney, Agent, or Firm*—Cooper & Dunham LLP

[57] ABSTRACT

A protein which inhibits Epidermal Growth Factor-induced cellular proliferation is disclosed, also a method of producing the protein in virus-infected host cells, including purifying the protein such as by using C18 reverse phase HPLC. Additionally, therapeutic uses of the protein also are described.

8 Claims, 4 Drawing Sheets

OTHER PUBLICATIONS

Ennis, B. W., Valverius, E. M., Bates, S. E., Lippman, M. E., Bellot F., Kris, R., Schlessinger, J., Masui, H., Goldenberg, A., Mendelsohn, J., Dickson, R. B.: Anti–Epidermal Growth Factor Receptor Antibodies Inhibit the Autocrine–Stimulated Growth of MDA–468 Human Breast Cancer Cells. *Molec. Endocrinol.* (1989), 3:1830–1838.

Elizalde, P. V., Charreau, E. H.: Alpha–Transforming Growth Factor Like Activities and Bifunctional Regulators of Cell Growth in Human Malignant Neoplasms. *Cancer Invest.* (1990), 8:365–374.

Matsunami, R. K., Campion, S. R., Niyogi, S. K., Stevens, A.: Analogs of Human Epidermal Growth Factor Which Partially Inhibit the Growth Factor–Dependent Protein–Tyrosine Kinase Activity of the Epidermal Growth Factor Receptor. *FEBS Letters* (1990), 264:105–108.

Eppstein, D. A., Marsh, Y. V., Schryver, B. B., Bertics, P. J.: Inhibition of Epidermal Growth Factor/Transforming Growth Factor–α–Stimulated Cell Growth by a Synthetic Peptide. *J. Cell. Physiol.* (1989), 141:420–430.

Strayer, D. S., Leibowitz, J. L.: Inhibition of Epidermal Growth Factor–Induced cellular Proliferation. *Am. J. Pathol.* (1987), 128:203–209.

Strayer, D. S., Skaletsky, E., Cabirac, G., Sharp, P. A., Corbeil, L. B., Sell, S., Leibowitz, J. L.: Malignant Rabbit Fibroma Virus Causes Secondary Immunosuppression in Rabbits. *J. Immunol.* (1983), 130:399–404.

Twardzik, D. R., Brown, J. P., Ranchalis, J. E., Todaro, G. J., Moss, B.: Vaccinia Virus–Infected Cells Release a Novel Polypeptide Functionally Related to Transforming and Epidermal Growth Factors. *Proc. Natl. Acad. Sci.* (1985) 83:5300–5304.

Stroobant, P., Rice, A. P., Gullick, W. J., Cheng, D. J., Kerr, I. M., Waterfield, M. D.: Purification and Characterization of Vaccinia Virus Growth Factor. *Cell*, (1985), 42:383–393.

Towbin, H., Staheiln, T., Gordon, J.: Electrophoretic Transfer of Proteins from Polyacrylamide Gels to Nitrocellulose Sheets: Procedure and Some Applications. *Proc. Natl. Acad. Sci.* (1979) 76:4350–4354.

Matsudaira, P.: Sequence from Picomole Quantities of Proteins Electroblotted Onto Polyvinylidene Difluoride Membranes. *J. Biol. Chem.* (1987), 261:10035–10038.

Pearson, W. R., Lipman, D. J.: Improved Tools for Biological Sequence Comparison. *Proc. Natl. Acad. Sci.* (1988), 85:2444–2448.

Drivas, G. T., Shih, A., Coutavas, E., Rush, M. G., D'Eustachio, P.: Characterization of Four Novel ras–Like Genes Expressed in a Human Teratocarcinoma Cell Line. *Mol. Cell. Biol.* (1990), 10:1793–1798.

Bischoff, F. R., Ponstingl, H.: Catalysis of Guanine Nucleotide Exchange on Ran by the Mitotic Regulator RCC1. *Nature* (1991), 354:80–82.

Downward, J., Parker, P., Waterfield, M. D.: Autophosphorylation Sites on the Epidermal Growth Factor Receptor. *Nature* (1984), 311:483–485.

Ahn, N. G., Weiel, J. E., Chan, C. P., Krebs, E. G.: Identification of Multiple Epidermal Growth Factor–Stimulated Protein Serine/Threonine Kinases from Swiss 3T3 Cells. *J. Biol. Chem.* (1990), 265:11487–11494.

Ahn, N. G., Krebs, E. G.: Evidence for an Epidermal Growth Factor–Stimulated Protein Kinase Cascade in Swiss 3T3 Cells. *J. Biol. Chem.* (1990), 265:11495–11501.

EPIDERMAL GROWTH FACTOR INHIBITOR

BACKGROUND OF THE INVENTION

Throughout this application various publications are referenced by arabic numerals within parenthesis. Full citations for these references may be found at the end of the specification immediately preceding the claims. The disclosures of these publications in their entireties are hereby incorporated by reference into this application in order to more fully describe the state of the art as known to those skilled therein as of the date of the invention described and claimed herein.

Rapid cell proliferation, in vivo, is responsible for a wide variety of conditions in mammals, including particularly humans, such as carcinomas, sarcomas, tumors, warts, papillomas, psoriasis and keloid scars. There is a continuing need for control and inhibition of such rapid cell proliferation in mammals, particularly human beings.

A number of growth factors which cause rapid cell proliferation are known. Such growth factors include transforming growth factor (TGF), nerve growth factor (NGF) and epidermal growth factor (EGF).

EGF is known to be a prototype for a family of cytokines which are recognized by Epidermal Growth Factor Receptor (EGFR) and which share general similarities in structure.

The present invention was examined in connection with EGF. However, it is anticipated that the present invention is applicable to cellular proliferation facilitated by any member of the EGF family.

EGF's roles in normal physiology and oncogenesis are not clear (1). However, it is known to target both epithelial and stromal cells and to stimulate epithelial growth (2,3).

Cell activation in response to EGF is facilitated by a specific receptor that recognizes it. After binding EGF, the external domain of EGFR undergoes conformational changes (4), leading to phosphorylation of EGFR cytoplasmic domain. Cell activation follows.

Several types of inhibitors of EGF activity have been reported. Some such inhibitors are structurally unrelated to EGF or EGFR, such as cyclosporin A, interferon-$^Y$, chrysarobin and TGFβ (5, 6). Prostaglandin and some anti-EGFR monoclonal antibodies and phorbol esters also are known to inhibit stimulation of certain target cells by EGF (6, 7, 8, 9). Several monoclonal anti-EGFR antibodies inhibit EGF-dependent growth of a human breast carcinoma cell line in vitro (10).

EGF-like proteins and peptides have also been used to inhibit growth stimulation of target cells by EGF. Small proteins that compete with EGF for EGFR, and mimic EGF activity on target cells have been identified in two human tumors (11). Engineered mutants of EGF are associated with decreased EGF-stimulated tyrosine kinase activity (12). It has been reported that a synthetic peptide encompassing the third disulfide loop of TGFα inhibits EGFR-related growth of human mammary carcinoma cells, although proliferation stimulated by fibroblast or platelet derived growth factors was unaltered (13).

Several years ago, there was described a protein that appeared to alter the ability of target cells to respond to EGF. Strayer, D. S. et al, Inhibition of Epidermal Growth Factor - Induced Cellular Proliferation, Am. J. Pathol. 128: 203–209 (1987).

Heretofore, production and purification methods for, therapeutic uses of, and useful compositions containing, this protein, referred to herein as EGF inhibitor (EGFI) have not been available.

SUMMARY OF THE INVENTION

One object of the present invention is to provide an epidermal growth factor inhibitor which inhibits rapid cellular proliferation.

In accordance with the present invention epidermal growth factor inhibitor is produced by infection of cells with virus, maintaining the cells in a suitable medium under suitable conditions, lysing of the cells, filtration and mixture with 1:1 methanol, removal of precipitates by centrifugation, and collection of the resulting supernatant.

Another object of the present invention is to provide a method for purifying epidermal growth factor inhibitor.

In accordance with the present invention, epidermal growth factor inhibitor is purified using C18 reverse phase HPLC, wherein a flow rate of 1 ml/min is maintained as the gradient proceeds from 100% solvent A (50% water: 49.9% methanol: 0.1% trifloroacetic acid (TFA) to 90% solvent B (99.9% acetonitrile: 0.1% TFA) in 60 minutes. Effluent from the column was analyzed using LKB Instruments diode array detector, scanning from 190 to 310 nm at 5 sec. intervals. Like fractions from sequential runs are pooled, solvents removed and proteins redissolved in saline. Relevant proteins are separated by preparative electrophoresis. Preparative SDS-PAGE is then used. Protein is recovered from the individual bands in the gel by electroelution, followed by resuspension in saline.

Still another object of the invention is to provide compositions and treatments employing same for the treatment of conditions characterized by rapid cell proliferation.

Yet another object of the invention is to provide methods for delivery of epidermal growth factor inhibitor topically, enterically, transdermally and systemically.

DETAILED DESCRIPTION OF THE INVENTION

RK-13 rabbit kidney cells were received from W. A. Tompkins, University of Illinois, Urbana, Ill. NRK cells, clone 49F, were purchased from American Type Culture Collection. A431 squamous carcinoma cells were the kind gift of Dr. Gordon Gill, University of California, San Diego. Techniques for passaging these cells have already been described (14, 15). Where reported, cell viability was determined by trypan blue exclusion.

Malignant rabbit fibroma virus was used. Its preparation, culture and storage are described elsewhere (15).

An assay of the ability of EGFI to inhibit EGF-induced cellular proliferation was described previously. Strayer, D. S. et al, Inhibition of Epidermal Growth Factor - Induced Cellular Proliferation, 1987 Am. J. Pathol. 128:202–209. In summary, NRK cells were passaged as usual until 1 day before the assay. At that time, they were transferred to Costar 24-well culture dishes in Dulbecco's modified Eagle's Medium (DMEM) with 0.5% Fetal Bovine Cell Serum (FCS). The following day, cells were washed with DMEM without serum and cultured with or without added EGF, EGFI or other supplement for 4–5 days. 24-hour incorporation of $^3$H-thymidine was measured by adding 5 μCi $^3$H-thymidine to each 1 cm$^2$ culture well, then harvesting the cells and counting incorporated radionucleotide one day later.

Established protocols used to purify EGF were used as guides in devising an approach to purifying EGFI (16,17). Rabbit kidney cell line RK-13 cells were infected with malignant Rabbit Fibroma Virus (MV) at a multiplicity of infection (MOI) of 3.0 in serum-free medium. After 36 hours, medium was removed and the cells washed with saline, then frozen, thawed and sonicated. This lysed cell preparation was filtered and mixed 1:1 with 100% methanol. This step precipitates about 90% of the protein in these preparations. Precipitates were removed by centrifugation.

Each application of the protein-containing sample in 50% methanol to the 1x25 cm semipreparative Supelco C18 reverse phase high pressure liquid chromatography (HPLC) column involved 10 mg total protein. A flow rate of 1 ml/minute was maintained as the gradient proceeded from 100% solvent A (50% water: 49.9% methanol: 0.1% triflouroacetic acid (TFA) to 90% solvent B (99.9% acetonitrile: 0.1% TFA) in 60 minutes. Effluent from the column was analyzed using LKB instruments a diode array detector, scanning from 190 to 310 nm at 5 sec. intervals.

Following this gradient, like fractions from sequential runs were pooled, solvents removed and proteins redissolved in saline. These were added to cultures of NRK cells as described, to identify the fractions(s) with EGFI activity.

The fractions showing EGFI activity contained two detectable proteins. They were separated by preparative electrophoresis. Initial work involved separation by agarose gel electrophoresis. However, subsequently preparative SDS-PAGE was used. Before electrophoresis, proteins were boiled for 8 min. in the presence of 4 mmol/L 2-mercaptoethanol and electrophoresed in gels containing SDS-10% polyacrylamide. Protein was recovered from the individual bands in the gel by electroelution, followed by resuspension in saline. Protein purity was ascertained by size exclusion chromatography using a LKB Instruments TSK4000 column.

Sequence analysis.

Preliminary analysis showed EGFI N-terminus to be blocked. Thus, the proteins were purified by SDS-PAGE and transferred to nitrocellulose (18), from which tryptic digestion was performed and these tryptic fragments isolated and sequenced (19).

Sequence information from the purified proteins was compared with protein sequences entered in GenBank using the FastaServe algorithm (20).

Protein phosphorylation after exposure to EGF, EGFI.

NRK or A431 cells were cultured as usual. On the day before the assay, the cells were transferred to Costar 6 well cluster dishes in serum-free medium. On the day of the assay, medium was changed, and cells were grown for 3 hours in normal saline supplemented with glucose and essential amino acids. EGF and/or EGFI were then added, and at various time intervals thereafter, 50 μCl $^{32}$PO$_4$. Cells were incubated with radiolabeled phosphate for 30 min., then washed extensively with normal saline and lysed with NS-1% Nonidet (Shell Chemical Corp.). Protein was precipitated by adding equal volumes of 15% trichloroacetic acid (TCA), washed with 10% TCA in water, resuspended in saline and analyzed by SDS-PAGE. Aliquots of protein precipitate were counted in a Beckmann Instruments scintillation counter.

Protein Production.

Cells were incubated in 24-well cluster dishes with leucine-free DMEM-0.5% dialyzed fetal bovine serum with or without added EGF (5 ng/ml) or EGFI (50 ng/ml). After various time periods, 10 μCi of $^3$H-leucine was added. One hour later, cultures were terminated by washing the adherent cells exhaustively with normal saline, lysing with water-0.1% SDS, and adding an equal amount of 15% TCA. Precipitated proteins were washed in 10% TCA, resuspended in saline, and protein-incorporated radioactivity counted. Parallel cultures were performed to measure viable cell recovery.

In addition, proteins from each culture time and condition were electrophoresed with SDS-PAGE. Gels were dried and autoradiographed.

Glucose and Lactate Determinations.

One ml aliquots of culture supernatants from cultures of NRK and A431 cells with or without EGF, EGFI and EGFI were harvested and their glucose (hexokinase technique, Hitachi 717) and lactate (LDH technique, Dupont aca II) measured by automated analyzers.

Purification of EGFI.

Figure 1A:
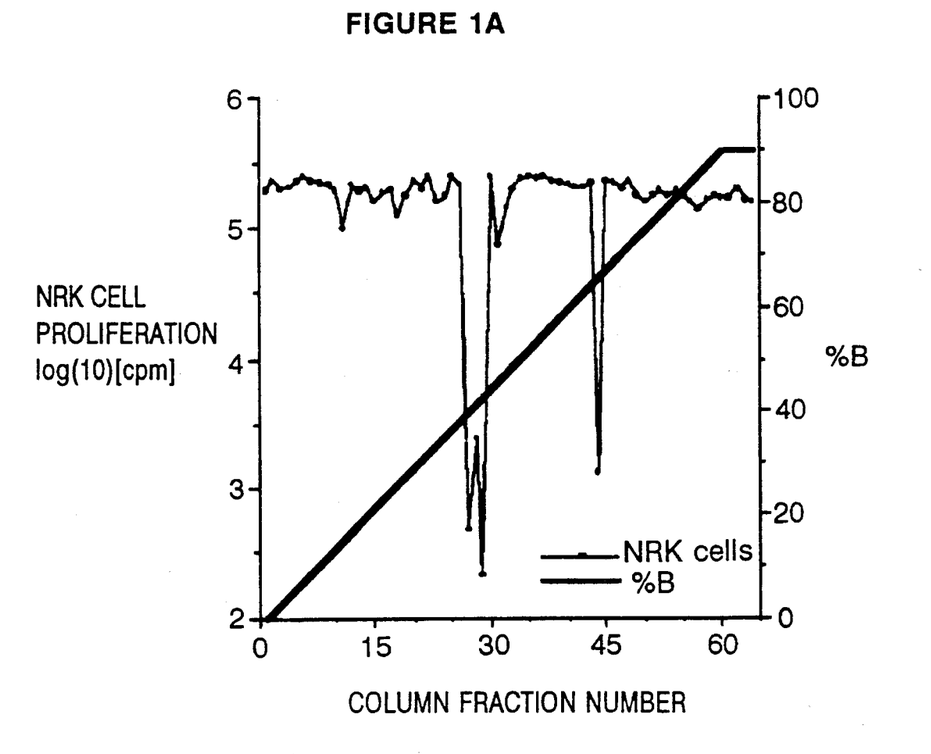
FIG. 1A Inhibition of NRK cell proliferation by column fractions from C18 RP column FIG. 1B Inhibition of A431 cell proliferation by column fractions from C18 RP column FIG. 2 Inhibition of EGF-stimulated proliferation of NRK cells.
Figure 1B:
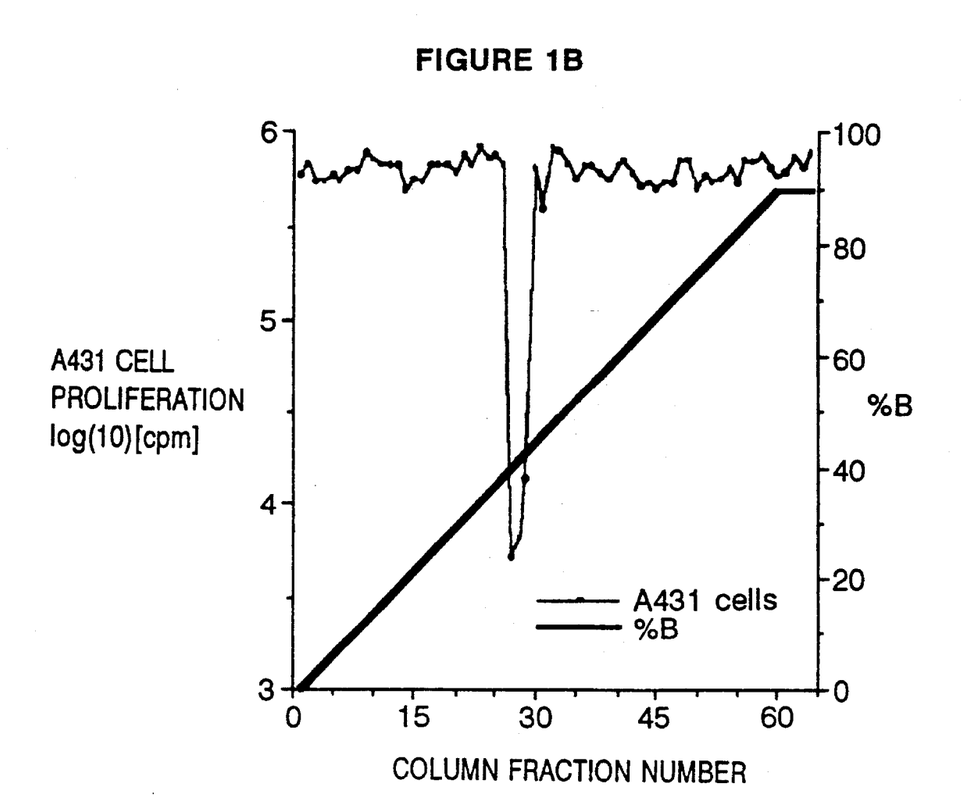

Crude lysates of RK-13 cells that inhibited EGF responses of NRK cells were eluted from an RP-HPLC gradient that went from 50% water-49.9% methanol; 0.1% TFA to 89.9% acetonitrile-5% water-5% methanol-0.1% TFA. Fractions were collected and solvents removed. Proteins were redissolved in normal saline and assayed for their ability to alter proliferation of EGF-response NRK cells and EGFR-bearing A431 cells. As seen in FIGS. 1A and 1B, inhibition of EGF-induced NRK cellular proliferation corresponded to a small number of fractions eluting at about 30% solvent B.

Fractions containing EGF inhibitory activity were pooled and analyzed by SDS-PAGE. They contained two principal proteins: one of approximately 68 kDa (M$_T$) and the other 34 kDa.

These proteins were purified by electroelution from SDS-PAGE gels. Purity of resultant proteins was verified by gel filtration HPLC, analyzing effluent with a scanning diode array detector. Both proteins were found to be pure.

UV-visible absorption spectra (190–310 nm) examined during peak elution were found to be invariant throughout the elution time. As a second protein component would have a different absorption spectrum, inhomogeneity would be appear as difference in UV-visible absorption spectra compared at the beginning and at the end of the eluting peak. It follows that the 34 kDa band contains a single protein.

Protein Sequence Analysis of the two Components of the RP-HPLC Peak.

Following purification by gel electrophoresis an attempt was made to sequence the two components of the reverse phase peak that inhibits NRK cellular responses to EGF. The 68 kDa protein (p68) was sequenced for the following 10 amino acids: DTHKSEIAHR (SEQ ID NO: 1). Its sequence exhibited considerable homology to human and bovine preproalbumin sequences.

Attempts to sequence the 34 kDa protein (p34) directly were unsuccessful, indicating a blocked N-terminus. The 34 kDa band was excised from a nitrocellulose filter after SDS-PAGE separation from the larger protein, and digested with trypsin. Tryptic digestion products were eluted from a C18 RPHPLC column and two such fragments were sequenced (SEQ ID NO: 2-3). These sequences are shown in Table 1 below, which shows comparative amino acids sequences of two tryptic fragments of the 34 kDa EGF inhibitor (SEQ ID NO: 2–3), p21$^{ras}$ (SEQ ID NO: 4) and the updated (3/92) sequence for TC4 (SEQ ID NO: 5), obtained from GenBank. Residues where the two are identical are denoted by a vertical bar (1), while those where they differ are denoted by a *.

As can be seen from Table 1, the residues of this protein's tryptic fragments show striking homology to a 24 kDa protein identified originally as a ras-like protein identified as an mRNA in human teratocarcinoma cells (21, 22).

raphy. P34 altered protein phosphorylation in both NRK and A431 cells, whether EGF was present or not.

This difference was observed at all times from 0 to 12 hr. after EGF/EGFI addition. The distinctive patterns of alteration induced by EGFI were consistent from one time point to the next and were similar when the phosphorylated proteins from A431 and NRK cells were compared.

When $^{32}PO_4$ incorporation into protein was measured as a function of time after exposure to EGFI and/or EGF, it was discovered that levels of protein phosphorylation in NRK cells increased dramatically between 4 and 20 hours of

TABLE 1

```
p21^ras                                         M T E   Y K L V V V G A G G   V G K S A L T I G L
Human ras-like protein:                M A A Q G E P Q V Q   F K L V L V G D G G   T G K T T F V K R H
                                                                                                  |
E G F I                                                                                           H I Q N H F V D E Y D   P T I E D S Y R K Q   V V I D G E T C —L   L D I L D T A G Q E   E Y S A M R D Q Y M L T G E F E K K Y V   A T L G V E V H O L   V F H T N R G P I K   F V N W D T A G Q E   K F G G L R D G Y Y
| | | | | | | | *     *
L T G E F E K K T —   S (SEQ ID NO:2)

R T G E G F L C V F   A I N N T K S F E D   I H Q Y R E Q I K R   V K D S D D V P M V L V   G N K C D L A A R T

I Q A Q C A I I M E   D V T S R V T Y K N   V P N W H R D L V R   V C E N——I P I V L C   G N K V D I K D R K

V E S R Q A Q—D L A R   S Y G I P Y I E T S   A K T R Q G V E D A   F Y T L V R E I R I   Q H K L R K L N P P

V K——A K I S V F H R   K K N L Q Y Y D I S   A K S N Y N F E K P   F L W L A R K L I G   D P N L E F V A M P
                                                                  | | | |   | | | | | | | | | |
                                                                  K L I G   D P N L E F V A M P
D E S G P G C M S C   K C V L S (SEQ ID NO:4)

A L A P P E V V M D   P A L A A Q Y E H D   L E V A Q T T A L P   D E D D D L (SEQ ID NO:5)
| | | | | | | | | |   | | | | | | | | | |   | | |
A L A P P E V V M D   P A L A A Q Y E H D   L E V (SEQ ID NO:3)
```

Ability of p34 to Inhibit EGF Activity.

Figure 2:
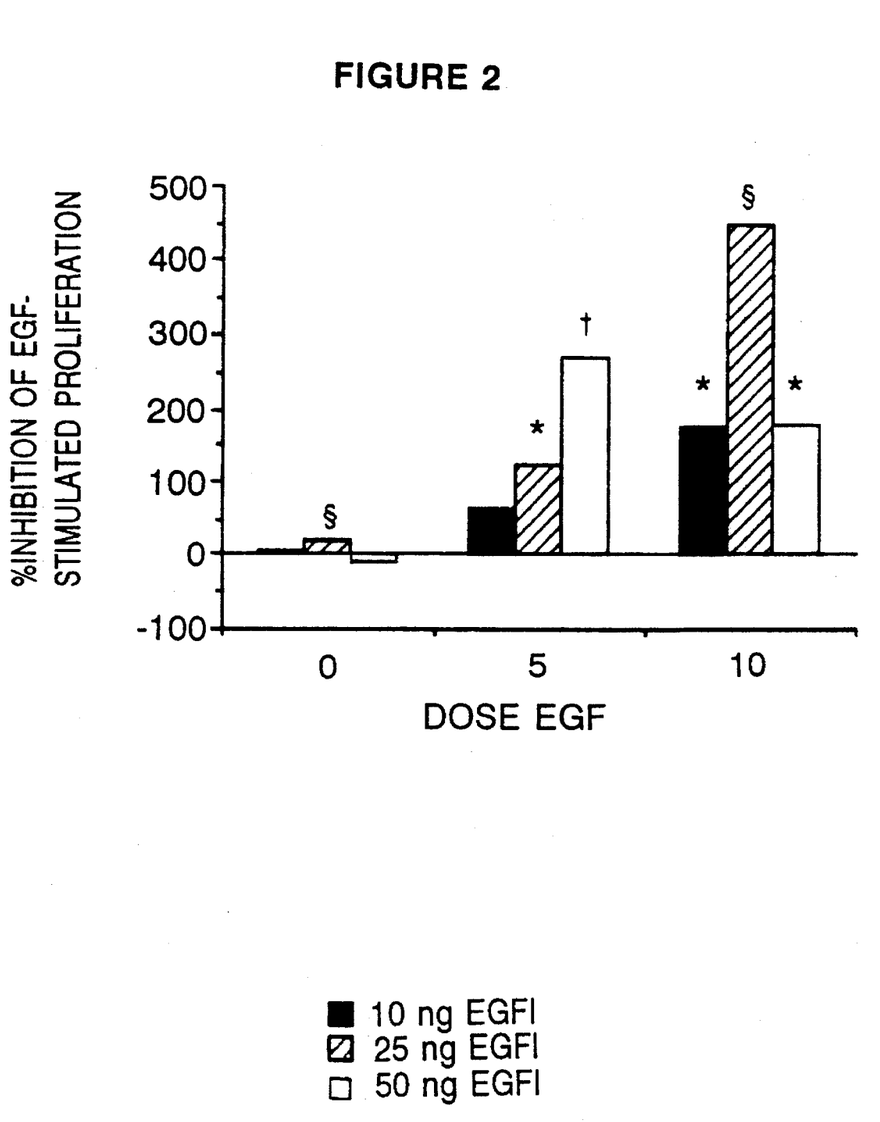

To determine whether p34 altered EGF-induced NRK cellular activation in vitro as an EGF inhibitor, EGF was added in 5 or 10 ng/ml concentrations to cultures of serum-starved NRK cells. Simultaneously, 10, 25, 50 ng/ml p34, purified as above, was added. In a dose dependent fashion, purified p34 completely inhibited EGF-stimulated NRK cell proliferation, as can be seen in FIG. 2.

At 10 and 25 ng/ml p34 also reduced unstimulated NRK proliferation to levels below the those observed without added EGF. Optimal inhibition was seen at approximately 25 ng/ml, depending on EGF concentration. Thus, p34 appears to inhibit EGF-induced cell proliferation (EGFI).

Figure 3:
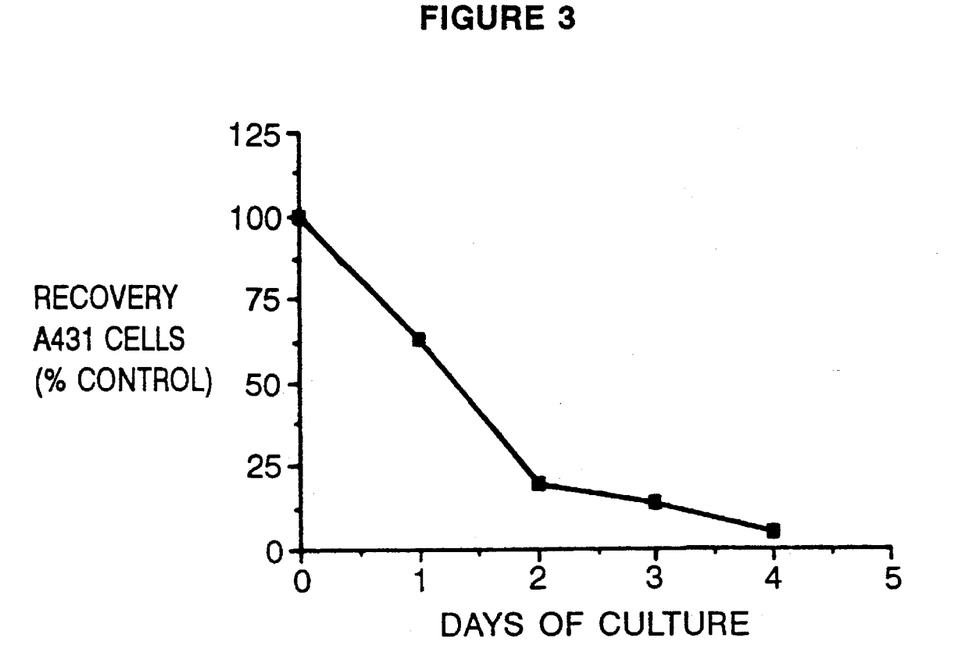
FIG. 3 Recovery of A431 cells cultured with 25 ng/ml EGFI.

The effects of p34 on A431 cells was even more surprising. 25–50 ng/ml of p34 caused A431 squamous carcinoma cells to lift off tissue culture dishes by 4–5 days of culture. Trypan blue exclusion was used to assess effects of p34 on A431 cell recovery in vitro. By five days after adding p34 very few viable A431 cells were recovered, as shown in FIG. 3.

In contrast, A431 cells cultured without p34 continue to proliferate.

Effects of p34 on protein phosphorylation.

Phosphorylation of cytoplasmic proteins is an important step in cellular activation following EGF and TGFα interaction with EGFR (23, 24, 25). We examined the effects of p34 on protein phosphorylation in EGF-stimulated and unstimulated NRK and A431 cells. EGF-(5 ng/ml) and/or EGFI (50 ng/ml) were added to cells in serum-free and phosphate free medium. $^{32}PO_4$ (50µ Cl/ml) was added at various times. Cells were harvested 30 minutes after addition of $^{32}PO_4$ and analyzed by SDS-PAGE and autoradiogculture. At all times, NRK cells cultured with EGFI incorporated significantly less $^{32}PO_4$ into protein that did control cells incubated without EGFI.

At all time points after 2 hours of incubation, cells incubated with EGF and EGFI incorporated less $^{32}PO_4$ than did control cells exposed only to EGF.

The effects of EGFI on protein phosphorylation in A431 cells were less consistent than those in NRK cells, although adding EGFI caused substantial differences in incorporated $^{32}PO_4$ at several time points. Generally, A431 cells incubated with EGFI, with or without EGF, phosphorylated less protein than did control A431 cells.

Effects of EGFI on Aspects of Cellular Metabolism.

To determine whether exposure to EGFI altered protein production and glucose utilization, EGFI was added to cultures of NRK and A431 cells, with and without EGF, and these parameters were measured at selected times thereafter. Data were corrected for cell number and, in the case of glucose and lactate determinations, total protein.

To measure protein production as a function of EGFI exposure, A431 and NRK cells were incubated in leucine-free medium with or without EGF and/or EGFI. At various times after culture initiation 3H-leu was added to the culture medium and cells harvested one hour later. Both EGF and EGFI stimulated protein production moderately 2 days after culture initiation, but not significantly thereafter. The stimulatory effects of EGF and EGFI were not additive.

Despite increased protein synthesis as a whole, however, no change in the species of proteins produced was detected. $^3$H-leu-labeled proteins from NRK or A431 cultures were prepared as described above and electrophoresed in SDS- PAGE. After electrophoresis, gels were dried and autoradiographed.

There appears to be little difference in the major species of proteins produced on exposure to EGF and/or EGFI. The time of exposure to these cytokines did not alter the result. Those protein species produced by cells after 2 hours exposure to EGF and/or EGFI did not differ appreciably from those produced after 44 hours exposure.

Lactate production and glucose utilization were measured as well. Though absolute values for these indices differed significantly in EGF and EGFI treated cells compared to control cells, when these values were corrected for cell numbers and total protein content, these indices were found to be equivalent among all groups.

Clinical Uses of Epidermal Growth Factor Inhibitor

The Epidermal Growth Factor Inhibitor of this invention can reasonably be expected to have clinical use in the treatment of animals, particularly mammals, most particularly human beings since it has been shown above that in in vitro tests, the presence of Epidermal Growth Factor Inhibitor can markedly decrease or completely inhibit rapid cell proliferation induced by EGF.

The striking results of the in vivo tests described above demonstrate that the Epidermal Growth Factor Inhibitor described herein has utility in the treatment of disorders in animals, particularly humans, caused by EGF-related rapid cell proliferation. Such disorders include psoriasis, keloid scarring, warts, leukoplakia, keratoses, carcinomas, sarcomas and condylomas.

Several types of delivery systems and carriers are contemplated. There are no limitations on the nature of acceptable carriers so long as they are efficacious for their intended use and cannot degrade the activity of the epidermal growth factor inhibitor.

The first embodiment is topically for the elimination of conditions such as psoriasis, keloid scars, warts and keratoses. For topical application, epidermal growth factor inhibitor can be included in various pharmaceutically acceptable carriers and/or adjuvants such as ointments, lotions, salves or creams, preferably in combination with purified collagen. Epidermal growth factor inhibitor may also be impregnated into transdermal patches, plasters, and bandages, preferably in a liquid or semi-liquid form. Epidermal growth factor inhibitor also can be delivered in aqueous solution for injection directly into the afflicted area.

Another application is systemically for the reduction of existing tumors and the prophylaxis and inhibition of new tumor growth such as carcinomas, sarcomas, tumors of the hematopoetic system, germ cell tumors and benign proliferations of these same cell types regardless of the organ of origin. When administered systemically, epidermal growth factor inhibitor may be formulated into liquids, tablets, pills and the like for enteral administration or in liquid form for injection.

Another application is for treatment of disorders of the mucous membranes of the body, including the upper respiratory system, the mouth and pharynx, the external coverings of the eye, the lower female genital tract and the anus. Such disorders include leukoplakia and leukioplakia vulvae. Epidermal growth factor inhibitor can be formulated into mouthwashes, rinses, sprays, creams, ointments and salves, designed to be used in affected mucous membranes.

The Epidermal Growth Factor Inhibitor of this invention is also usefully combined in compositions containing antiviral components, such as adenine arabinoside and/or antineoplastic components, such as adriamycin or cytoxan and/or antimicrobial agents, e.g. antibiotics and the like.

It should be appreciated that the specification depicts presently preferred embodiments of the invention. Other changes and modifications may be made, as would be apparent to those skilled in the art, without departing from the spirit and scope of the invention.

References

1. Laurence, D. J. R., Gusterson, B. A.: The epidermal growth factor. *Tumor Biol.*, 1990, 11:229–261.

2. Coleman, S., Silberstein, G. B., Daniel, C. W.: Ductal morphogenesis in the mouse mammary gland: evidence supporting a role for epidermal growth factor. *Dev. Biol.*, 1988, 127:304–315.

3. Taub, M., Wang, Y., Szcaesny, T. M., Kleinman, H. K.: Epidermal growth factor or transforming growth factor α is required for kidney tubulogenesis in matrigel cultures in serum-free medium, 1990, *Proc. Natl. Acad. Sci.* (U.S.A.), 87:4002–4006.

4. Greenfield, C., Hiles, I., Waterfield, M. D., Federwisch, M., Wollmer, A., Blundell, T. L., McDonald, N.: Epidermal growth factor binding induces a conformational change in the external domain of its receptor. 1989, *EMBO J.*, 8:4115–4123.

5. Nickoloff, B. J., Mitra, R. S.: Inhibition of $^{125}$I-epidermal growth factor binding to cultured keratinocytes by antiproliferative molecules gamma interferon, cyclosporin A, and transforming growth factor-beta. 1989, *J. Invest. Dermatol.* 93:799–803.

6. Imamoto, A., Beltran, L. M., DiGiovanni, J.: Differential mechanism for the inhibition of epidermal growth factor binding to its receptor on mouse keratinocytes by anthrones and phorbol esters. 1990, *Carcinogenesis* 11:1543–1549.

7. Hori, T., Kashiyama, S., Hayakawa, M., Shimbamoto, S., Tsujimoto, M., Oku, N., Ito, F.: Possible role of prostaglandins as negative regulators in growth stimulation by tumor necrosis factor and epidermal growth factor in human fibroblasts. 1989, *J. Cell. Physiol.* 141:275–280.

8. Murthy, U., Rieman, D. J., Rodeck, U.: Inhibition of TGF alpha-induced second messengers by anti-EGF receptor antibody-425. 1990, *Biochem. Biphys. Res. Comm.* 172:471–476.

9. Rodeck, U., Williams, N., Murthy, U., Herlyn, M.: Monoclonal antibody 425 inhibits growth stimulation of carcinoma cells by exogenous EGF and tumor-derived EGF-TGF-alpha. 1990, *J. Cell. Biochem.* 44:69–79.

10. Ennis, B. W., Valverius, E. M., Bates, S. E., Lippman, M. E., Bellot F., Kris, R., Schlessinger, J., Masui, H., Goldenberg, A., Mendelsohn, J., Dickson, R. B.: Anti-epidermal growth factor receptor antibodies inhibit the autocrine-stimulated growth of MDA-468 human breast cancer cells. 1989, *Molec. Endocrinol.* 3:1830–1838.

11. Elizalde, P. V., Charreau, E. H.: Alpha-transforming growth factorlike activities and bifunctional regulators of cell growth in human malignant neoplasms. 1990, *Cancer Invest.* 8:365–374.

12. Matsunami, R. K., Campion, S. R., Niyogi, S. K., Stevens, A.: Analogs of human epidermal growth factor which partially inhibit the growth factor-dependent protein-tyrosine kinase activity of the epidermal growth factor receptor. 1990, *FEBS Letters* 264:105–108.

13. Eppstein, D. A., Marsh, Y. V., Schryver, B. B., Bertics, P. J.: Inhibition of epidermal growth factor/transforming growth factor-α-stimulated cell growth by a synthetic peptide. 1989, *J. Cell. Physiol.* 141:420–430.

14. Strayer, D. S., Leibowitz, J. L.: Inhibition of epidermal growth factor-induced cellular proliferation. 1987, *Am. J. Pathol.* 128:203–209.

15. Strayer, D. S., Skaletsky, E., Cabirac, G., Sharp, P. A., Corbeil, L. B., Sell, S., Leibowitz, J. L.: Malignant rabbit fibroma virus causes secondary immunosuppression in rabbits. 1983. *J. Immunol.* 130:399–404.

16. Twardzik, D. R., Brown, J. P., Ranchalis, J. E., Todaro, G. J., Moss, B.: Vaccinia virus-infected cells release a novel polypeptide functionally related to transforming and epidermal growth factors. 1985, *Proc. Natl. Acad. Sci.* (USA), 82:5300–5304.

17. Stroobant, P., Rice, A. P., Gullick, W. J., Cheng, D. J., Kerr, I. M., Waterfield, M. D.: Purification and characterization of vaccinia virus growth factor. 1985, *Cell*, 42:383–393.

18. Towbin, H., Staheiln, T., Gordon, J.: Electrophoretic transfer of proteins from polyacrylamide gels to nitrocellulose sheets: Procedure and some applications. 1979, *Proc. Natl. Acad. Sci.* (U.S.A.) 76:4350–4354.

19. Matsudaira, P.: Sequence from picomole quantities of proteins electroblotted onto polyvinylidene difluoide membranes. 1987, *J. Biol. Chem.*, 261:10035–10038.

20. Pearson, W. R., Lipman, D. J.: Improved tools for biological sequence comparison. 1988, *Proc. Natl. Acad. Sci.* (U.S.A.), 85:2444–2448.

21. Drivas, G. T., Shih, A., Coutavas, E., Rush, M. G., D'Eustachio, P.: Characterization of four novel ras-like genes expressed in a human teratocarcinoma cell line. 1990, *Mol. Cell. Biol.*, 10:1793–1798.

22. Bischoff, F. R., Ponstingl, H.: Catalysis of guanine nucleotide exchange on Ran by the mitotic regulator RCC1. 1991, *Nature*, 354:80–82.

23. Downward, J., Parker, P., Waterfield, M. D.: Autophosphorylation sites on the epidermal growth factor receptor. 1984, *Nature*, 311:483–485.

24. Ahn, N. G., Weiel, J. E., Chan, C. P., Krebs, E. G.: Identification of multiple epidermal growth factor-stimulated protein serine/theonine kinases from Swiss 3T3 cells. 1990, *J. Biol. Chem.* 265:11487–11494.

25. Ahn, N. G., Krebs, E. G.: Evidence for an epidermal growth factor-stimulated protein kinase cascade in Swiss 3T3 cells. 1990, *J. Biol. Chem.* 265:11495–11501.

---

I claim:

1. A method of producing an epidermal growth factor inhibitor which inhibits Epidermal Growth Factor-induced cellular proliferation which comprises the steps of:
   infecting host kidney cells with a fibroma virus to produce infected cells;

disrupting the infected cells to form a mixture;

filtering the mixture to remove cellular debris;

adding an equal amount of 100% methanol to the mixture such that the final concentration of methanol is 50% of the mixture so as to form a precipitate;

removing the precipitate from the mixture by centrifugation; and collecting the mixture containing said epidermal growth factor inhibitor.

2. The method of claim 1 where the host cells are mechanically disrupted.

3. The method of claim 1 wherein the host cells are RK-13 rabbit kidney cells.

4. The method of claim 1 wherein the virus is Malignant Rabbit-Fibroma Virus.

5. A method of recovering purified Epidermal Growth Factor Inhibitor produced by the method of claim 1 comprising the steps of:

passing the epidermal growth factor inhibitor-containing mixture through a semi-preparative C18 reverse phase HPLC column, wherein a flow rate of 1 ml/min is maintained along a gradient from 100% solvent A (50% water: 49.9% methanol: 0.1% trifluoroacetic acid (TFA) to 90% solvent B (99.9% acetonitrile: 0.1% TFA) in 60 minutes;

analyzing effluent from the C18 column using a diode array detector, scanning from 190 to 310 nm at 5 second intervals;

pooling like fractions from sequential runs; removing solvents;

redissolving a resulting 34 KDa protein in saline;

separating said 34 KDa protein by preparative gel electrophoresis;

recovering said 34 KDa protein from the electrophoresis gel by electroelution;

and resuspending said 34 KDa protein in saline.

6. A method of obtaining purified epidermal growth factor inhibitor from a sample, comprising;

a) loading the sample onto a reverse phase HPLC column;

b) eluting the sample from the reverse phase HPLC column with a gradient which proceeds from about fifty percent methanol in aqueous solution to about ninety percent acetonitrile;

c) determining a fraction having epidermal growth factor inhibiting activity;

d) collecting said fraction having epidermal growth factor inhibiting activity;

e) electrophoresing the fraction in an electrophoresis medium; and f) recovering a protein having a molecular weight of about 34 kilodaltons from the electrophoresis medium.

7. The method of claim 6 wherein the electrophoresis medium is a sodium dodecyl sulfate-polyacrylamide gel.

8. The method of claim 6 wherein the recovering comprises electroeluting.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: unknown
        ( D ) TOPOLOGY: linear     ( i i ) MOLECULE TYPE: protein     ( i i i ) HYPOTHETICAL: N     ( i v ) ANTI-SENSE: N     ( v ) FRAGMENT TYPE: internal     ( x i ) SEQUENCE DESCRIPTION: SEQ ID NO:1:

```
Asp  Thr  His  Lys  Ser  Glu  Ile  Ala  His  Arg
1                   5                        10
```

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: unknown
        ( D ) TOPOLOGY: linear     ( i i ) MOLECULE TYPE: protein     ( i i i ) HYPOTHETICAL: N     ( i v ) ANTI-SENSE: N     ( v ) FRAGMENT TYPE: internal     ( x i ) SEQUENCE DESCRIPTION: SEQ ID NO:2:

```
His  Leu  Thr  Gly  Glu  Phe  Glu  Lys  Lys  Thr  Ser
1                   5                        10
```

( 2 ) INFORMATION FOR SEQ ID NO:3:

( i ) SEQUENCE CHARACTERISTICS:
( A ) LENGTH: 37 amino acids
( B ) TYPE: amino acid
( C ) STRANDEDNESS: unknown
( D ) TOPOLOGY: linear ( i i ) MOLECULE TYPE: protein ( i i i ) HYPOTHETICAL: N ( i v ) ANTI-SENSE: N ( v ) FRAGMENT TYPE: internal ( x i ) SEQUENCE DESCRIPTION: SEQ ID NO:3:

```
Lys Leu Ile Gly Asp Pro Asn Leu Glu Phe Val Ala Met Pro Ala Leu
1               5                   10                  15

Ala Pro Pro Glu Val Val Met Asp Pro Ala Leu Ala Ala Gln Tyr Glu
            20              25                  30

His Asp Leu Glu Val
        35
```

( 2 ) INFORMATION FOR SEQ ID NO:4:

( i ) SEQUENCE CHARACTERISTICS:
( A ) LENGTH: 190 amino acids
( B ) TYPE: amino acid
( C ) STRANDEDNESS: unknown
( D ) TOPOLOGY: linear ( i i ) MOLECULE TYPE: protein ( i i i ) HYPOTHETICAL: N ( i v ) ANTI-SENSE: N ( v ) FRAGMENT TYPE: internal ( x i ) SEQUENCE DESCRIPTION: SEQ ID NO:4:

```
Met Thr Glu Tyr Lys Leu Val Val Val Gly Ala Gly Gly Val Gly Lys
1               5                   10                  15

Ser Ala Leu Thr Ile Gly Leu Ile Gln Asn His Phe Val Asp Glu Tyr
            20              25                  30

Asp Pro Thr Ile Glu Asp Ser Tyr Arg Lys Gln Val Val Ile Asp Gly
            35              40                  45

Glu Thr Cys Leu Leu Asp Ile Leu Asp Thr Ala Gly Gln Glu Glu Tyr
    50              55                  60

Ser Ala Met Arg Asp Gln Tyr Met Arg Thr Gly Glu Gly Phe Leu Cys
65              70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100             105                 110

Leu Val Gly Asn Lys Cys Asp Leu Ala Ala Arg Thr Val Glu Ser Arg
            115             120                 125

Gln Ala Gln Asp Leu Ala Arg Ser Tyr Gly Ile Pro Tyr Ile Glu Thr
    130             135                 140

Ser Ala Lys Thr Arg Gln Gly Val Glu Asp Ala Phe Tyr Thr Leu Val
145             150                 155                 160

Arg Glu Ile Arg Ile Gln His Lys Leu Arg Lys Leu Asn Pro Pro Asp
                165                 170                 175
```

-continued

| | | | | | | | | | | | | | |
|---|---|---|---|---|---|---|---|---|---|---|---|---|---|
| Glu | Ser | Gly | Pro | Gly | Cys | Met | Ser | Cys | Lys | Cys | Val | Leu | Ser |
| | | | 180 | | | | | 185 | | | | | 190 |

( 2 ) INFORMATION FOR SEQ ID NO:5:

( i ) SEQUENCE CHARACTERISTICS:
      ( A ) LENGTH: 216 amino acids
( B ) TYPE: amino acid
( C ) STRANDEDNESS: unknown
( D ) TOPOLOGY: linear ( i i ) MOLECULE TYPE: protein ( i i i ) HYPOTHETICAL: N ( i v ) ANTI-SENSE: N ( v ) FRAGMENT TYPE: internal ( x i ) SEQUENCE DESCRIPTION: SEQ ID NO:5:

| | | | | | | | | | | | | | | | |
|---|---|---|---|---|---|---|---|---|---|---|---|---|---|---|---|
| Met | Ala | Ala | Gln | Gly | Glu | Pro | Gln | Val | Gln | Phe | Lys | Leu | Val | Leu | Val |
| 1 | | | | 5 | | | | | 10 | | | | | 15 | |
| Gly | Asp | Gly | Gly | Thr | Gly | Lys | Thr | Thr | Phe | Val | Lys | Arg | His | Leu | Thr |
| | | | 20 | | | | | 25 | | | | | 30 | | |
| Gly | Glu | Phe | Glu | Lys | Lys | Tyr | Val | Ala | Thr | Leu | Gly | Val | Glu | Val | His |
| | | 35 | | | | | 40 | | | | | 45 | | | |
| Pro | Leu | Val | Phe | His | Thr | Asn | Arg | Gly | Pro | Ile | Lys | Phe | Val | Asn | Trp |
| | 50 | | | | | 55 | | | | | 60 | | | | |
| Asp | Thr | Ala | Gly | Gln | Glu | Lys | Phe | Gly | Gly | Leu | Arg | Asp | Gly | Tyr | Tyr |
| 65 | | | | | 70 | | | | | 75 | | | | | 80 |
| Ile | Gln | Ala | Gln | Cys | Ala | Ile | Ile | Met | Glu | Asp | Val | Thr | Ser | Arg | Val |
| | | | | 85 | | | | | 90 | | | | | 95 | |
| Thr | Tyr | Lys | Asn | Val | Pro | Asn | Trp | His | Arg | Asp | Leu | Val | Arg | Val | Cys |
| | | | 100 | | | | | 105 | | | | | 110 | | |
| Glu | Asn | Ile | Pro | Ile | Val | Leu | Cys | Gly | Asn | Lys | Val | Asp | Ile | Lys | Asp |
| | | 115 | | | | | 120 | | | | | 125 | | | |
| Arg | Lys | Val | Lys | Ala | Lys | Ile | Ser | Val | Phe | His | Arg | Lys | Lys | Asn | Leu |
| | 130 | | | | | 135 | | | | | 140 | | | | |
| Gln | Tyr | Tyr | Asp | Ile | Ser | Ala | Lys | Ser | Asn | Tyr | Asn | Phe | Glu | Lys | Pro |
| 145 | | | | | 150 | | | | | 155 | | | | | 160 |
| Phe | Leu | Trp | Leu | Ala | Arg | Lys | Leu | Ile | Gly | Asp | Pro | Asn | Leu | Glu | Phe |
| | | | | 165 | | | | | 170 | | | | | 175 | |
| Val | Ala | Met | Pro | Ala | Leu | Ala | Pro | Pro | Glu | Val | Val | Met | Asp | Pro | Ala |
| | | | 180 | | | | | 185 | | | | | 190 | | |
| Leu | Ala | Ala | Gln | Tyr | Glu | His | Asp | Leu | Glu | Val | Ala | Gln | Thr | Thr | Ala |
| | | 195 | | | | | 200 | | | | | 205 | | | |
| Leu | Pro | Asp | Glu | Asp | Asp | Asp | Leu | | | | | | | | |
| | 210 | | | | | 215 | | | | | | | | | |